(12) United States Patent
Chilian et al.

(10) Patent No.: US 11,911,384 B2
(45) Date of Patent: *Feb. 27, 2024

(54) VASODILATORS FOR TREATMENT OF HEART FAILURE

(71) Applicant: NORTHEAST OHIO MEDICAL UNIVERSITY, Rootstown, OH (US)

(72) Inventors: William M. Chilian, Atwater, OH (US); Vahagn Ohanyan, Hudson, OH (US); Liya Yin, Hudson, OH (US)

(73) Assignee: NORTHEAST OHIO MEDICAL UNIVERSITY, Rootstown, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/739,629

(22) Filed: May 9, 2022

(65) Prior Publication Data

US 2023/0093487 A1    Mar. 23, 2023

Related U.S. Application Data

(63) Continuation of application No. 16/606,451, filed as application No. PCT/US2018/028871 on Apr. 23, 2018, now Pat. No. 11,324,748.

(60) Provisional application No. 62/596,290, filed on Dec. 8, 2017, provisional application No. 62/488,300, filed on Apr. 21, 2017.

(51) Int. Cl.
| | | |
|---|---|---|
| *A61K 31/519* | (2006.01) | |
| *A61P 9/08* | (2006.01) | |
| *A61K 9/00* | (2006.01) | |
| *A61K 31/353* | (2006.01) | |

(52) U.S. Cl.
CPC .......... *A61K 31/519* (2013.01); *A61K 9/0019* (2013.01); *A61K 9/0053* (2013.01); *A61K 31/353* (2013.01); *A61P 9/08* (2018.01)

(58) Field of Classification Search
CPC ............................ A61K 31/353; A61K 31/519
See application file for complete search history.

(56) References Cited

U.S. PATENT DOCUMENTS

| 11,324,748 B2 * | 5/2022 | Chilian .................... A61P 9/08 |
| 2006/0018970 A1 | 1/2006 | Bristow |
| 2011/0082084 A1 | 4/2011 | Szeto |
| 2013/0225530 A1 | 8/2013 | Li-Weber |
| 2015/0366901 A1 | 12/2015 | Chirinos |
| 2017/0056356 A1 | 3/2017 | Rajasekhar |

FOREIGN PATENT DOCUMENTS

| WO | 2011038298 A1 | 3/2011 |
| WO | 2015177378 A1 | 11/2015 |

OTHER PUBLICATIONS

PCT International Search Report for corresponding International Application Serial No. PCT/US2018/028871, dated Aug. 9, 2018.
Hariri, Lana and Patel, Jayesh "Vasodilators", StatPearls, Jul. 9, 2021.
Tarkin, Jason M. and Kaski, Juan Carlos "Vasodilator Therapy: Nitrates and Nicorandil." Cardiovascular Drugs and Therapy, vol. 30, No. 4, Aug. 2017, pp. 367-378 doi:10.1007/s10557-016-6668-z.
Fine, Nowell; Merck Manual: Heart Failure (HF) [online] retrieved from: https://www.merckmanuals.com/home/heart-and-blood-vessel-disorders/heart-failure/heart-failure-hf#; 16 pages (2020).
Bhuiyan et al., Heart Failure with Preserved Ejection Fraction: Persisten Diagnosis, Therapeutic Enigma, Curr Cardiovasc Risk Rep. vol. 5(5), pp. 440-449, (2011).
Guarini, Giacinta et al. "Microvascular function/dysfunction downstream a coronary stenosis." Current pharmaceutical design vol. 19,13 (2013): 2366-74. doi:10.2174/1381612811319130004.
Maher, Abdul R et al. "Hypoxic modulation of exogenous nitrite-induced vasodilation in humans." Circulation vol. 117,5 (2008): 670-7. doi:10.1161/CIRCULATIONAHA.107.719591.
EP Search Report dated Dec. 14, 2020 for corresponding EP application No. 18787308.8.
Dong et al., "Takotsubo Syndrome is a Coronary Microvascular Disease: Experimental Evidence," European Heart Journal, Jun. 21, 2023, 44(24):2244-2253, https://doi.org/10.1093/eurheartj/ehad274.

\* cited by examiner

*Primary Examiner* — Deepak R Rao
(74) *Attorney, Agent, or Firm* — TAROLLI, SUNDHEIM, COVELL & TUMMINO L.L.P.

(57) ABSTRACT

A method for treating or preventing heart failure involving blockage of small blood vessels is described. The method involves administering to a subject in need thereof a therapeutically effective amount of a vasodilator.

18 Claims, 10 Drawing Sheets

VASODILATORS FOR TREATMENT OF HEART FAILURE

CROSS-REFERENCE TO RELATED APPLICATIONS

This application claims priority to U.S. Provisional Application Ser. No. 62/026,239, filed on Apr. 21, 2017, and U.S. Provisional Application Ser. No. 62/596,290, filed on Dec. 13, 2017, both of which are hereby incorporated by reference in their entirety.

GOVERNMENT FUNDING

This invention was made with government support under Grant No. HL832387 awarded by the National Institutes of Health. The government has certain rights in this invention.

BACKGROUND

Heart failure (HF) is one of the major cardiovascular health problems afflicting our society. According to the National Heart Lung Blood Institute, in the United States HF occurs in nearly 1.8% of the total population, which translates into about 5 million cases. Patients with congestive heart failure have a 25% mortality rate within 3 years. Perhaps the most sobering statistic is that there are no cures for heart failure and the current treatments merely slow the progression of the disease, adding about 3 years to life expectancy. Current therapies for heart failure are directed at reducing myocardial oxygen demands. These therapies are designed to decrease wall stress, and thus chamber radius by decreasing preload using aldosterone antagonists, reducing preload and afterload with AT1 receptor antagonists or ACE inhibitors, or by decreasing heart rate and cardiac contractility using β-adrenergic antagonists. It is understandable why reductions in myocardial oxygen demands are targeted in the situation of a weakened heart. However, given the fact that progression of the disease is only slowed, one cannot help but wonder whether the correct mechanism targeted. If the correct mechanism were targeted, could the progression of the disease be stopped or reversed, rather than merely being slowed?

A classic observation in heart failure is that the myocardium is characterized by diffuse fibrosis, which is referred to as "replacement fibrosis." Dai et al., J Cardiol., 60:416-21 (2012); Passino et al., Clin Chim Acta, 443:29-38 (2015) It is somewhat enigmatic that ischemia is rarely mentioned in the discussion of what causes the fibrosis and most discussion in the literature centers around a decrease in capillary density. Mohammed et al., Circulation, 131:550-9 (2015). Some groups have proposed growth factor therapies to stimulate angiogenesis in the failing heart (Gogiraju et al., Cardiovasc Res., 111:204-16 (2016)); and the converse has been observed in patients, i.e., anti-angiogenic therapies used to treat cancer appear to increase the risk for heart failure. Qi et al., Clin Drug Investig., 34:681-90 (2014). Although myocardial blood flow is controlled by coronary resistance vessels, if there is overt rarefaction of capillaries, oxygen delivery to cardiac myocytes will be hampered. Although these observations are consistent with the idea that heart failure is caused by a perfusion deficit, they do not directly test this hypothesis; in fact, it could be argued that if the control of flow is abnormal, increasing the number of capillaries would not have a positive effect. Another observation is that patients with impairments in coronary vasodilator reserve, in the absence of large vessel coronary disease, have an increased incidence of heart failure. Takashio et al., J Am Coll Cardiol., 62:632-40 (2013). Again, this reveals an association but not "cause and effect." The need remains for a method of treating heart failure that has the potential to provide a longer-term cure for heart failure.

SUMMARY OF THE INVENTION

If insufficient perfusion is at the root of certain types of heart failure, then increased myocardial blood flow to the failing heart will prevent ischemia and rescue cardiac function in the failing heart. Heart failure with reduced ejection fraction (HFrEF) is a classification of heart failure denoting reduced ventricular systolic function, leading to insufficient pumping action and inadequate cardiac output to supply the needs of the body. This type of failure progresses to pulmonary congestion and ultimately death. Although in some instances the cause of the failure is known, e.g., mutation in a contractile protein, under most conditions the failure is of unknown etiology. A typical characteristic in patients with HFrEF is diffuse fibrosis of the left ventricle, which suggests that during the evolution of the disease, there has been a loss of cardiac myocytes, with their replacement by fibrotic tissue. The inventors hypothesize that the cause of the loss of cardiac myocytes is insufficient myocardial blood flow to meet the needs of the heart, and this imbalance between myocardial blood flow and cardiac metabolism leads to minute areas of ischemia, myocyte loss, and fibrosis culminating in HFrEF. To test this hypothesis, they determined the relationship between myocardial blood flow (MBF) and cardiac work (CW) in control, wild type mice (Cont) and wild type mice with TAC (to produce heart failure [HF]) during a cardiac stress test (norepinephrine-induced changes in cardiac work in anesthetized animals 12-13 weeks post TAC). Cardiac work was determined from the product of left ventricular wall stress and heart rate (wall stress rate product [WSRP]). The data shows the relationship between cardiac work (WSRP) and MBF in WT Cont (WT) and HF mice. Based on these findings, the inventors propose that a cause of HFrEF is inadequate MBF to meet the metabolic demands of the working heart, and that this insufficiency ultimately leads to death of cardiac myocytes and heart failure.

The current therapies for heart failure, specifically HFrEF, only slow the progression of the disease. Although these standard of care therapies are used to treat HFpEF, INOCA, MINOCA, diabetic and doxorubicin-induced cardiomyopathy and Takotsubo Syndrome, there is no evidence they produce any benefit. In fact, clinical trials to date aimed at treating HFpEF using the therapies for HFrEF have failed. The present invention provides an effective treatment for heart failure involving the blockage of small blood vessels, including the conditions of INOCA, MINOCA, HFpEF, diabetic and doxorubicin-induced cardiomyopathy, and Takotsubo Syndrome, all of which otherwise lack an effective treatment.

BRIEF DESCRIPTION OF THE FIGURES

The present invention may be more readily understood by reference to the following figures, wherein.

DETAILED DESCRIPTION OF THE INVENTION

Figure 1:
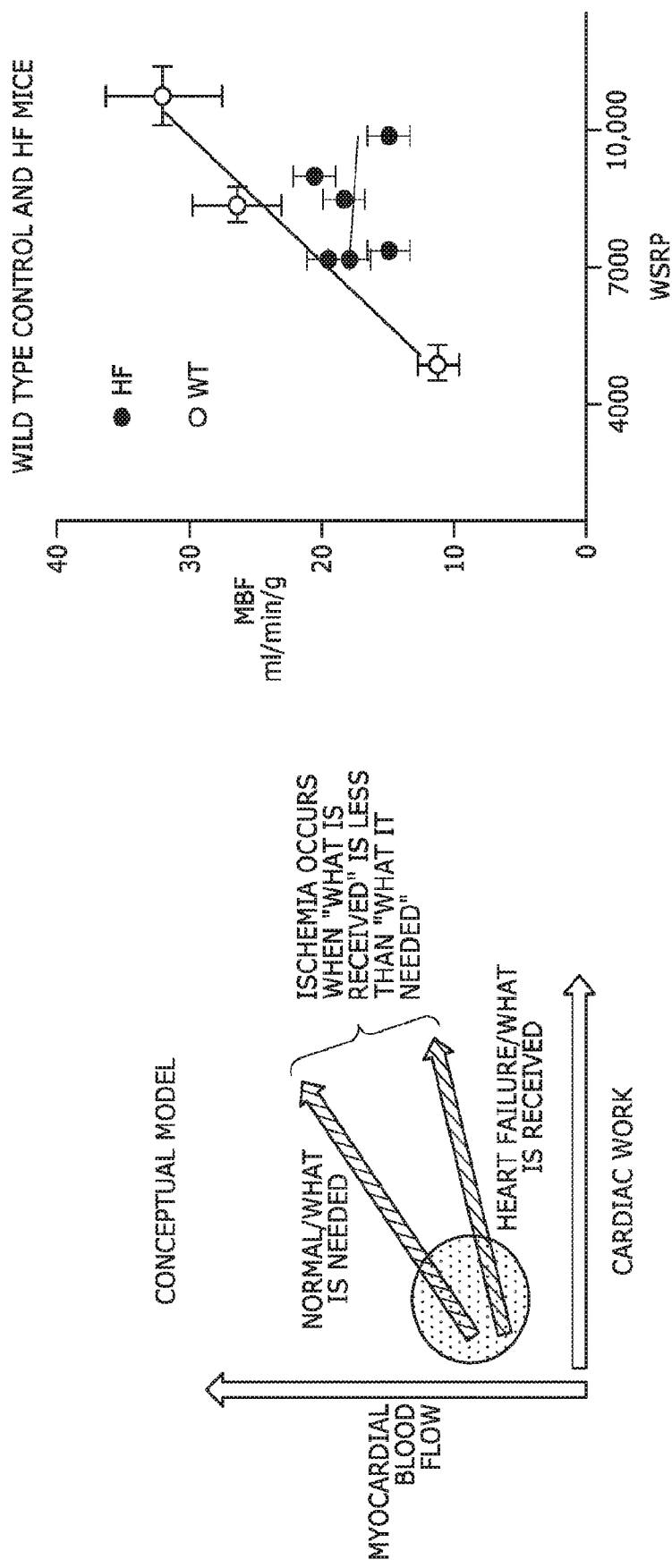
FIG. 1 provides graphs, with the left graph showing the conceptual relationship between myocardial blood flow and cardiac work in heart failure, while the right graph shows the relationship between the Wall Stress Rate Product (WSRP) and MBF in WT Sham (WT; n=4) and WT mice in heart failure (HF; n=4). Note the relationship between MBF and cardiac work (WSRP) is blunted in the failing heart, i.e., for any given level of work, MBF is less in HF than in the control, and that this difference is magnified at higher levels of work.

The present invention relates to methods for treating or preventing heart failure involving blockage of small blood vessels. The methods involve administering to a subject in need thereof a therapeutically effective amount of a vasodilator.

Definitions

As used herein, the term "heart failure" is broadly used to mean any condition in which the function of the heart is inadequate to meet the systemic needs of the metabolic, whether the impaired function is due to reduced contraction (systolic dysfunction) or due to reduce relaxation (diastolic dysfunction). In both conditions, diastolic pressures in the heart increase, resulting in congestion and edema in the tissues. Most frequently, heart failure is caused by decreased contractility of the myocardium, resulting from MI or reduced coronary blood flow; however, many other factors may result in heart failure, including damage to the heart valves, vitamin deficiency, and primary cardiac muscle disease.

The term "treatment," "treating," or other equivalents encompasses the amelioration, cure, maintenance (i.e., the prevention of relapse), improvement, and/or reversal of the symptoms of a cardiovascular disease or pathological condition being treated. Treatment after a disease or disorder has started or manifested aims to reduce, ameliorate, or altogether eliminate the disorder, and/or its associated symptoms, to prevent it from becoming worse, or to prevent the disorder from re-occurring once it has been initially eliminated (i.e., to prevent a relapse). In certain embodiments, treatment does not include prevention.

In the case of treating heart failure, treatment may include the improvement and/or reversal of the diminished ability of the heart to pump blood or its impaired relaxation. Improvement in the physiologic function of the heart may be assessed using any of the measurements described herein (e.g., measurement of ejection fraction, fractional shortening, left ventricular internal dimension, heart rate, etc.), as well as any effect upon the animal's survival.

Prevention, as used herein, refers to any action providing a benefit to a subject at risk of being afflicted with a condition or disease such as heart failure, including avoidance of or a decrease of one or more symptoms of the disease should heart failure occur.

"Pharmaceutically acceptable" as used herein means that the compound or composition is suitable for administration to a subject for the methods described herein, without unduly deleterious side effects in light of the severity of the disease and necessity of the treatment.

As used herein, the term "diagnosis" can encompass determining the likelihood that a subject will develop a disease, or the existence or nature of disease in a subject. The term diagnosis, as used herein also encompasses determining the severity and probable outcome of disease or episode of disease or prospect of recovery, which is generally referred to as prognosis). "Diagnosis" can also encompass diagnosis in the context of rational therapy, in which the diagnosis guides therapy, including initial selection of therapy, modification of therapy (e.g., adjustment of dose or dosage regimen), and the like.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

Unless defined otherwise, all technical and scientific terms used herein have the same meaning as commonly understood by one of ordinary skill in the art to which this invention belongs.

Treatment of Heart Failure

In one aspect, the present invention provides a method for treating heart failure involving blockage of small blood vessels. The method includes administering to a subject in need thereof a therapeutically effective amount of a vasodilator.

Vasodilators

Endogenous substances and drugs that cause dilation of blood vessels are termed vasodilators. When blood vessels dilate, the flow of blood is increased due to a decrease in vascular resistance. A variety of different types of vasodilators are known to those skilled in the art. Types of vasodilators include nonsympatholytic vasodilators, peripheral vasodilators, and coronary vasodilators. Vasodilators operate through a variety of different mechanisms. Examples of vasodilators classified by mechanism include angiotensin converting enzyme inhibitors, angiotensin receptor blockers, calcium channel blockers, and nitrates, which donate nitric oxide that stimulates the soluble form of the enzyme guanylate cyclase in the smooth muscle cells of blood vessels.

In some embodiments, the vasodilator comprises a coronary vasodilator. Coronary vasodilators are preferred because their effects are more focused on the heart, and therefore the likelihood of undesirable side-effects is decreased. Non-limiting examples of coronary vasodilators include amotriphene, bendazol, benfurodil hemisuccinate, benziodarone, chloracizine, chromonar, cinepazet, clobenfurol, clonitrate, cloridarol, dilazep, dipyridamole, droprenilamine, efloxate, erythrityl tetranitrane, efloxate, etafenone, fendiline, floredil, ganglefene, heptaminol, herestrol bis((3-diethylaminoethyl ether), hexobendine, imolamine, itramin tosylate, khellin, lidoflanine, linsidomine, mannitol hexanitrane, medibazine, molsidomine, nesiritide, nicorandil, nicorglycerin, oxyfedrin, pentaerythritol tetranitrate, pentrinitrol, perhexyline, pimethylline, prenylamine, serelaxin, trapidil, tricromyl, trimetazidine, trolnitrate phosphate and visnadine.

In some embodiments, the coronary vasodilator is chromonar or a chromonar derivative. Chromonar was once used to treat coronary artery disease. Gross et al., Gen Pharmacol., 12(3):199-204 (1981). However, it was withdrawn because of its very potent effect of increasing blood flow to the heart. Sometimes in patients with severe blockages in coronary arteries, a drug that increases blood flow to the heart will "steal" blood flow from the vessel with the blockage to increase flow in an adjacent region. This worsens the deficit in flow in the area of the heart supplied by the artery with the blockage. This phenomenon is called "coronary steal" and is the reason chromonar was discontinued. However, the inventors have determined that vasodilators, and in particular coronary vasodilators such as chromonar, are effective for treating heart failure that involves the blockage of small blood vessels.

The structure of chromonar is shown by formula I below. Chromonar is also known as carbocromen and intercordin, and has the chemical name 14.3-(beta-Diethylaminoethyl)-4-methyl-7-(carbethoxymethoxy)-coumarin hydrochloride. In some embodiments, chromonar derivatives can also be used as coronary vasodilators to treat heart failure involving the blockage of small blood vessels. Chromonar derivatives, as the term is used herein, are chroman derivatives as described by U.S. Pat. No. 5,719,155, the disclosure of which is incorporated herein by reference.

I

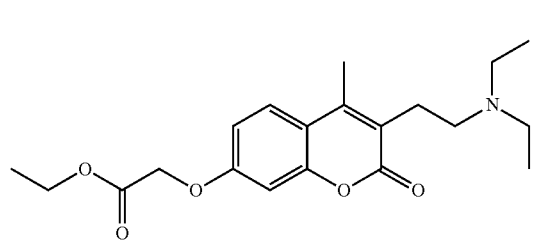

Coronary vasodilators such as chromonar increase blood flow to the heart without affecting blood flow to other organs like the brain, the gut, or skeletal muscle. This property makes vasodilators well-suited to treat conditions where blood flow to the heart is insufficient to meet its energy requirements. Normally, when the heart works harder, it receives more blood flow to enable increased delivery of oxygen and nutrients. This allows any increase in work to be balanced by an increase in flow. However, preclinical models of heart failure such Takotsubo syndrome and a newly named condition called INOCA (also known as MINOCA) all share a common link—insufficient blood flow to the heart. The inventors have also found that increasing blood flow to the heart with coronary vasodilators such as chromonar stops the progression of these diseases, and can even reverse some consequences of the disease.

While treatment or prevention can involve the use of other agents, in some embodiments, treatment consists of administration of the vasodilator without other agents (e.g., cardiovascular agents) being present, such that treatment consists essentially of administration of the vasodilator (e.g., coronary vasodilator). Exclusion of other agents does not exclude the presence of a pharmaceutically acceptable carrier, and therefore in some embodiments treatment consists or consists essentially of administration of the vasodilator together with a pharmaceutically acceptable carrier.

Heart Failure Involving Blockage of Small Blood Vessels

The present invention provides a method for treating heart failure involving blockage of small blood vessels. In most heart failure, the disease is not due to blockages in large arteries in the heart; rather the disease is due to a problem with the small blood vessels in the heart. Blockage, which involves excessive constriction and/or inadequate dilation of coronary blood vessels, leads to insufficient blood flow to the heart, which the inventors have found is the cause of a number of types of heart failure. In some embodiments, the heart failure involving blockage of small blood vessels being treated is non-ischemic heart failure, while in other embodiments, the heart failure being treated is heart failure that does not result from large vessel disease. Administration of the vasodilator can increase myocardial blood flow to the heart of the subject. Alternately, or in addition, administration of the vasodilator improves contractile function (ejection fraction) and/or cardiac relaxation of the subject.

Blood vessels transport blood throughout the body, and include arteries, veins, and capillaries. Small blood vessels include all blood vessels other than large blood vessels. Examples of small blood vessels include arterioles and capillaries. In some embodiments, small blood vessels are blood vessels having a diameter of 1.0 mm or less, while in other embodiments, small blood vessels include blood vessels having a diameter of 0.5 mm or less, 0.2 mm or less, or 0.1 mm or less.

In some embodiments, the heart failure being treated is non-ischemic heart failure. Heart failure can occur as a result of causes other than ischemia, and these types of heart failure are referred to herein as non-ischemic heart failure. Examples of non-ischemic heart failure include congestive heart failure, dilated cardiomyopathy, hypertrophic cardiomyopathy, restrictive cardiomyopathy, diabetic cardiomyopathy, amyloid cardiomyopathy, doxorubicin-induced cardiomyopathy, and arrhythmogenic right ventricular dysplasia (ARVD), myocarditis resulting from viral infection, amyloidosis of cardiac tissue, arrhythmia, manifestation of genetic defects, injury from abuse of alcohol (alcoholic cardiomyopathy), drugs, or cigarettes, other sources of injury to cardiac tissue such as infection by bacteria or parasites, or vitamin deficiency. Non-ischemic heart failure has a range of etiologies, including congenital, infectious agents (e.g., viral cardiomyopathy), autoimmune, and idiopathic causes.

In some embodiments, the heart failure being treated is a disease selected from the group consisting of Takotsubo Syndrome, diabetic cardiomyopathy, doxorubicin-induced cardiomyopathy, heart failure with preserved ejection fraction, ischemia with no coronary disease (INOCA) and myocardial infarction with non-obstructive coronary arteries (MINOCA). Doxorubicin-induced cardiomyopathy is an undesired side effect of doxorubicin administration. Doxorubicin is used to treat cancer, but its use is limited by the damage it produces in the heart. This damage leads to a type of heart failure called doxorubicin-induced cardiomyopathy, which constrains its use as an effective anti-cancer treatment.

Current treatments for heart failure, which are specific for HFrEF, only slow the progression of the disease. Moreover, no effective treatments for HFpEF, INOCA, MINOCA, Takotsubo Syndrome, and doxorubicin-induced and diabetic cardiomyopathy are currently used. Because a deficit in flow in the small blood vessel circulation (e.g., microcirculation) appears to be a common thread for all of these diseases, the use of coronary vasodilators such as chromonar should be an effective treatment for all of these conditions. If the progression of these chronic diseases can be stopped, and in some instances, reversed, the impact on the quality of life, and productivity will be greatly enhanced in patients afflicted with these diseases of the heart.

Vasodilators can be administered therapeutically to a subject that is already afflicted by heart failure involving the blockage of small blood vessels. In one embodiment of therapeutic administration, administration of the compounds is effective to eliminate the heart failure; in another embodiment, administration of the vasodilator is effective to decrease the severity of the heart failure or lengthen the lifespan of the subject so afflicted. In some embodiments, the method of treatment consists of administering a therapeutically effective amount of a vasodilator in a pharmaceutically acceptable formulation to the subject over a substantial period of time, such as a week, or month, at least 6 months, or at least 12 months.

A subject being treated for heart failure involving blockage of small blood vessels will typically exhibit manifestations of heart failure. The phrase "manifestations of heart failure" is used herein broadly to encompass all of the sequelae associated with heart failure, such as shortness of breath, pitting edema, an enlarged tender liver, engorged neck veins, pulmonary rales, decreased energy and fatigue, and the like including laboratory findings associated with heart failure. In some embodiments, the subject is suspected of having, or is diagnosed with, heart failure but is free of ischemic myopathy resulting from large vessel disease. In other embodiments, the subject is suspected of having, or is diagnosed with, heart failure, but is free of ischemic myopathy resulting from re-vascularized (treated) large vessel disease.

Prevention of Heart Failure

In another aspect, the invention provides a method for preventing heart failure involving blockage of small blood vessels. The method includes administering to a subject in need thereof a therapeutically effective amount of a vasodilator. Vasodilators can be administered prophylactically to a subject in advance of the occurrence of heart failure. Prophylactic (i.e., preventive) administration is effective to decrease the likelihood of the subsequent occurrence of heart failure in the subject, or decrease the severity of heart failure that subsequently occurs. A subject in need of prophylactic treatment can be a subject that is at elevated risk of developing heart failure, such as a subject having high blood pressure, diabetes, or a family history of heart failure.

Prophylactic treatment can be provided when the subject has been diagnosed as having one or more risk factors known to be associated with heart failure. For example, in some embodiments, a subject who has been diagnosed as suffering from blockage of small blood vessels proximal to the heart can be given prophylactic treatment. Blockage of small blood vessels proximal to the heart can be identified by, for example, a computed tomography scan, or angiography.

Preventing heart failure involving the blockage of small blood vessels can be carried out using the various vasodilators described herein, and can be used to prevent the various specific types of heart failure described herein. For example, in some embodiments, the vasodilator is a coronary vasodilator, while in further embodiments the coronary vasodilator is chromonar or dipyridamole. In some embodiments, the heart failure being prevented is non-ischemic heart failure, while in further embodiments the heart failure being prevented is a disease selected from the group consisting of Takotsubo Syndrome, diabetic cardiomyopathy, doxorubicin-induced cardiomyopathy, heart failure with preserved ejection fraction, ischemia with no coronary disease (INOCA) and myocardial infarction with non-obstructive coronary arteries (MINOCA).

Administration and Formulation

The present invention also provides pharmaceutical compositions that include a vasodilator as an active ingredient, and a pharmaceutically acceptable liquid or solid carrier or carriers, in combination with the active ingredient. Any of the vasodilators described herein as suitable for the treatment of heart failure, such as coronary vasodilators or a specific vasodilator such as chromonar can be included in pharmaceutical compositions of the invention.

The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, drip infusion, transdermal patch, or by direct injection into cardiac tissue. Typical forms of administration include oral and intravenous administration.

Pharmaceutical compositions comprising the subject agents may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. Nos. 6,416,510; 6,716,196; 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically acceptable salt refers to the relatively non-toxic, inorganic and organic acid addition salts of the compounds. These salts can be prepared in situ during the final isolation and purification of the compound, or by separately reacting a vasodilator compound with a suitable counterion and isolating the salt thus formed. Representative counterions include sodium, potassium, calcium, magnesium, ammonium, arginine, diethylamine, ethylenediamine, and piperazine salts, and the like. See for example Haynes et al., J. Pharm. Sci., 94, p. 2111-2120 (2005). For example, chromonar can be administered as chromonar hydrochloride.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, Remington's Pharmaceutical Sciences 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

An effective amount, also referred to as a therapeutically effective amount, of a subject agent or pharmaceutical composition thereof, is an amount sufficient to ameliorate at least one symptom associated with the cardiovascular disease or pathological condition. The therapeutically effective amount to be included in pharmaceutical compositions may depend, in each case, upon several factors, e.g., the type, size and condition of the patient to be treated, the intended mode of administration, the capacity of the patient to incorporate the intended dosage form, etc. One of ordinary skill in the art would be able to determine empirically an appropriate therapeutically effective amount.

While it is possible for the agents to be administered as the raw substances, it is preferable, in view of their potency, to present them as a pharmaceutical formulation. The formulations of the present invention for human use comprise the agent, together with one or more acceptable carriers therefor and optionally other therapeutic ingredients. The carrier(s) must be "acceptable" in the sense of being compatible with the other ingredients of the formulation and not deleterious to the recipient thereof or deleterious to the inhibitory function of the active agent. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier, which constitutes one or more accessory ingredients. In general, the formulations are prepared by uniformly and intimately bringing into association the agent with the carrier(s) and then, if necessary, dividing the product into unit dosages thereof.

Formulations suitable for parenteral administration conveniently comprise sterile aqueous preparations of the agents, which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization. Such formulations may optionally contain one or more additional ingredients among which may be mentioned preservatives, such as methyl hydroxybenzoate, chlorocresol, metacresol, phenol and benzalkonium chloride. Such materials are of special value when the formulations are presented in multidose containers.

Buffers may also be included to provide a suitable pH value for the formulation. Suitable such materials include sodium phosphate and acetate. Sodium chloride or glycerin may be used to render a formulation isotonic with the blood. If desired, the formulation may be filled into the containers under an inert atmosphere such as nitrogen or may contain an anti-oxidant, and are conveniently presented in unit dose or multi-dose form, for example, in a sealed ampoule.

The administration of the pharmaceutical composition or formulation to a patient can be intravenous, intraarterial, intraperitoneal, intramuscular, subcutaneous, intrapleural, intrathecal, by perfusion through a regional catheter, or by direct intralesional injection. When administering by injection, for example, the administration may be by continuous infusion, or by single or multiple boluses. The dosage may vary depending upon such factors as the patient's age, weight, gender, general medical condition, and previous medical history.

In some embodiments, it may be desirable to target delivery to the heart, while limiting delivery of the therapeutic to other organs. This may be accomplished by any one of a number of methods known in the art. In one embodiment delivery to the heart of a pharmaceutical formulation described herein comprises coronary artery infusion. In certain embodiments coronary artery infusion involves inserting a catheter through the femoral artery and passing the catheter through the aorta to the beginning of the coronary artery.

Examples have been included to more clearly describe particular embodiments of the invention. However, there are a wide variety of other embodiments within the scope of the present invention, which should not be limited to the particular example provided herein.

EXAMPLES

Example 1: Is Heart Failure a Coronary Microvascular Disease?

Currently heart failure is associated with several conditions: reduced cardiac function caused by myocardial infarction, mutations in contractile and structural proteins, and inflammation such as viral-induced myocarditis. Ajani et al., Cardiovasc Revasc Med., 7:234-6 (2006) Other than the mutations in the contractile and structural proteins, the exact cause of heart failure is not known. Even in the situation of heart failure occurring secondary to a myocardial infarction, the reason why the remaining viable myocardium eventually fails is obscure. Although the inventors do not ascribe to a "one solution" type answer, the fact that all types of heart failure are characterized by diffuse fibrosis and all benefit from a reduction in metabolic demands, they propose a conceptual explanation for several types of HF of unknown etiology in FIG. 1. The panel on the left is a conceptualization of how inadequate coupling between metabolism and flow leads to failure, i.e., the connection between cardiac work and myocardial blood flow is impaired so that the failing heart gets less perfusion than what it needs. The difference between these two lines is the perfusion deficit—representing ischemia—that the inventors hypothesize leads to failure. Note that as cardiac work increases, the perfusion deficit, i.e., level of ischemia, increases. The inventors believe that current therapies that are successful minimize the deficit by reducing cardiac work, which is represented by the blue circle. Note the perfusion deficit still remains but it is much smaller than that at high levels of work. This scheme was developed to explain why the current therapies only slow the progression of the disease. In the right panel are results that support this concept. Cardiac work in heart failure was estimated from the product of left ventricular wall stress and heart rate (wall stress-rate-product [WSRP]). Cardiac work (WSRP) was plotted versus myocardial blood flow in sham control and HF mice. The difference between the sham controls and the HF group is striking: metabolic dilation is severely compromised in the HF mice. As the level of work would increase, the degree of insufficient blood flow would increase. A reason that the current therapies designed to treat heart failure are effective in slowing the progression of the disease may be because they chronically reduce metabolic demands of the myocardium and as a result they minimize the perfusion deficit, i.e., the level of ischemia is reduced. Even with this therapy, there remains persistent myocardial ischemia, albeit at low levels, and this is why current treatments only slow the progression of the disease. The inventors concept for using a vasodilator such as chromonar to treat heart failure is that by increasing blood flow to the heart, heart failure can be stopped or even reversed by increasing blood flow to the heart and eliminating myocardial ischemia. The evidence for this is shown in FIGS. 2 and 3.

Figure 2:
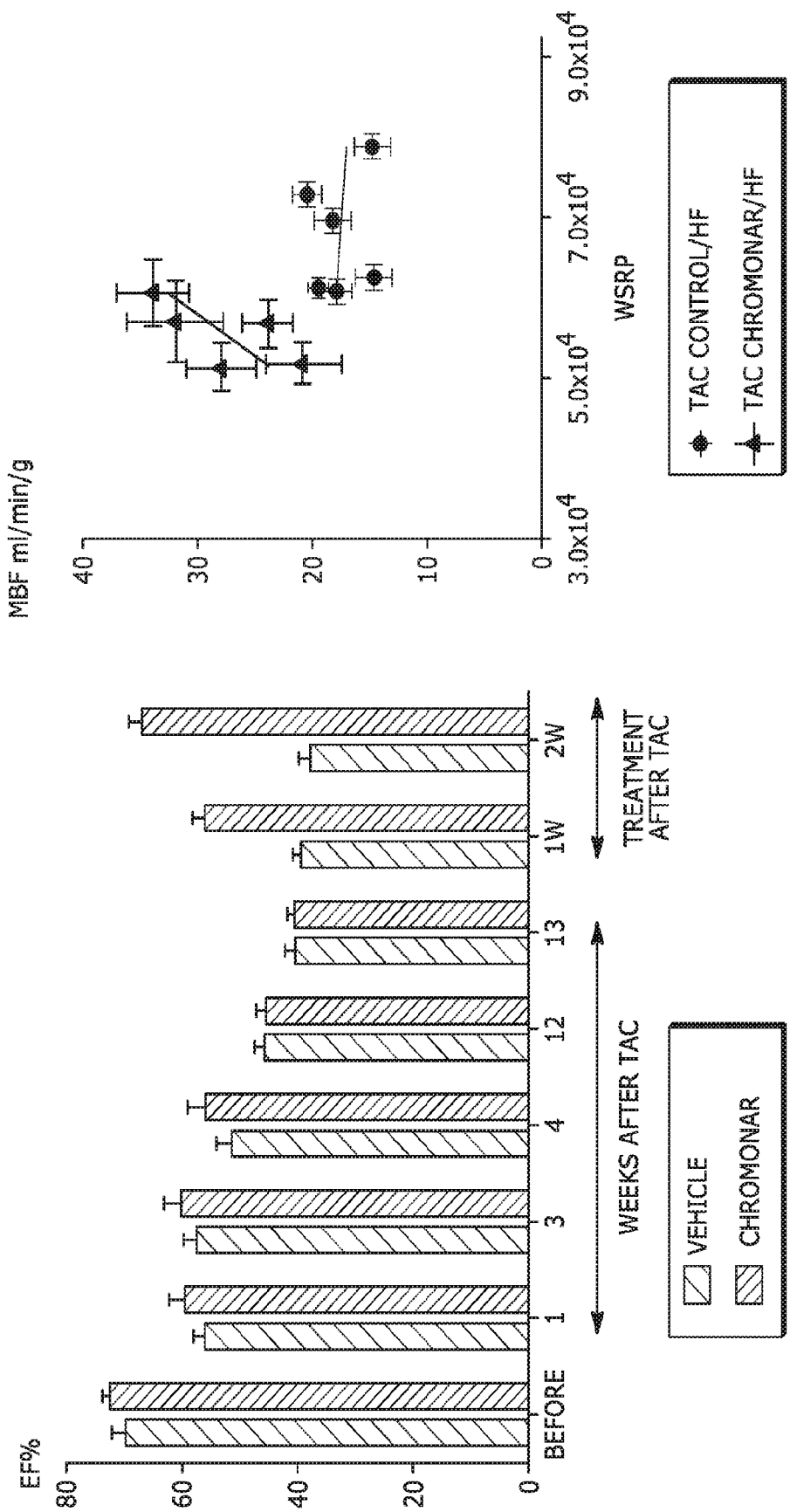
FIG. 2 provides graphs showing the effects of chromonar or vehicle treatment of Left Ventricular Ejection Fraction (% EF) in heart failure (HF) induced by transaortic constriction (TAC) (left) and on myocardial blood flow (MBF) during HF (right).
Figure 3:
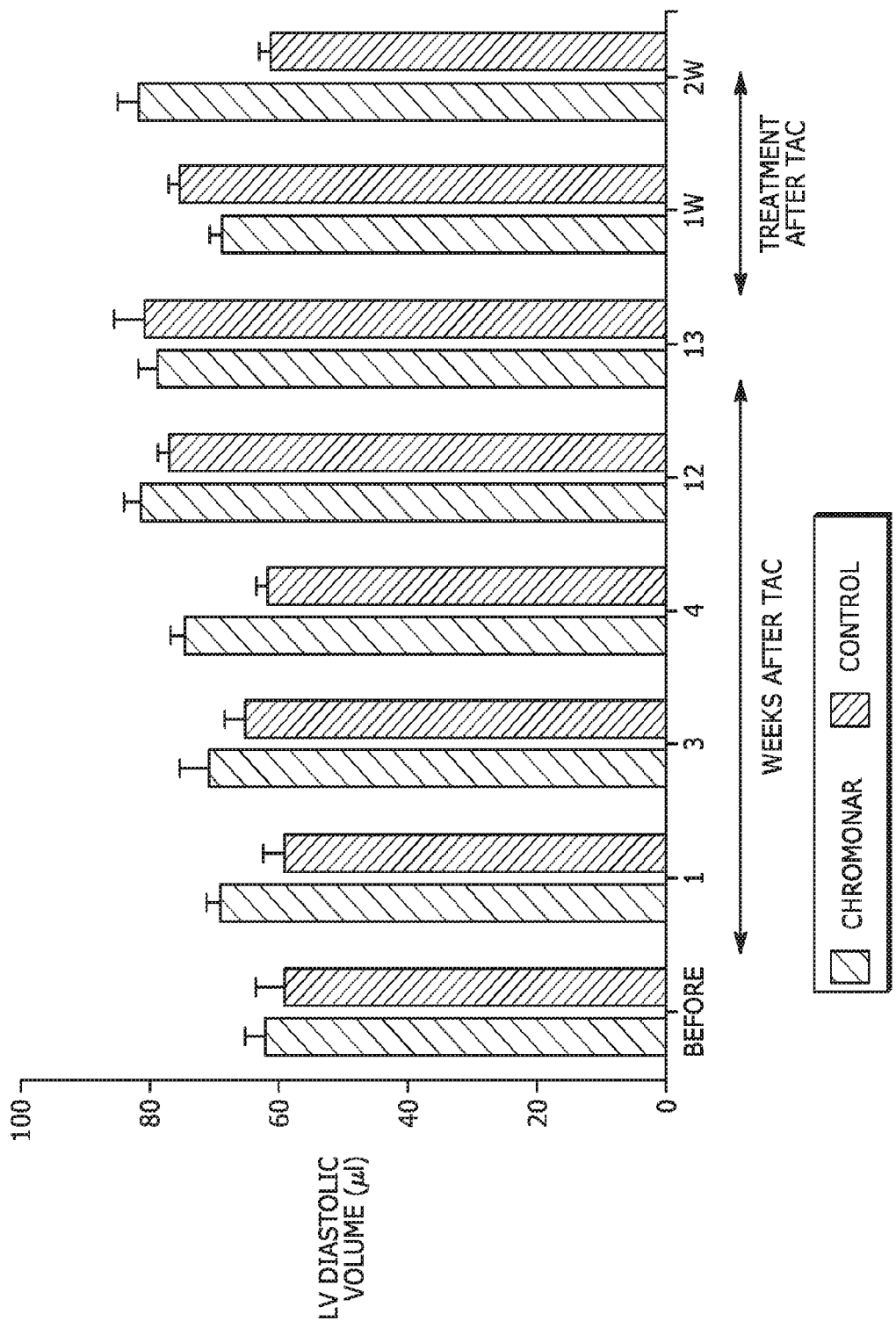
FIG. 3 provides a graph showing the effects of chromonar or vehicle (control) treatment on Left Ventricular Diastolic Volume in heart failure (HF) induced by Transaortic constriction (TAC).

FIG. 2 provides proof of principle for the concept that heart failure is caused by insufficient blood flow to the heart. The left panel shows an index of cardiac function (ejection fraction, % EF) in normal mice under control, baseline conditions (in the figure this is denoted as Before). Ejection fraction is the percentage of blood in the left ventricular chamber that the heart ejects per beat. Under normal conditions, the heart will eject 60-70% of left ventricular volume with each contraction, but the failing heart ejects considerably less. After the control measurements to establish baseline % EF, mice underwent surgery to constrict the aortic artery. This procedure, termed transaortic constriction (TAC), causes the heart to pump against a high blood pressure, which causes it to fail. This progression towards failure is evident in the left panel as shown by the deterioration in cardiac function in both groups of mice up to 13 weeks. At the end of the 13th week, mice were either treated with chromonar (as continuous infusion) or a vehicle (that the chromonar was dissolved in). Note, mice given chromonar had restored cardiac function—nearly back to the control levels occurring prior to the TAC. Also note the mice given vehicle had no such improvement. This shows that chromonar treatment improved cardiac function in the failing heart. To prove that this effect is mediated via an increase in blood flow to the heart (myocardial blood flow, MBF), the inventors measured blood flow to the heart during changes in cardiac work. The right panel of FIG. 2 provides further proof of principle for the concept that blood flow to the heart is insufficient in heart failure. The relationship between myocardial blood flow (MBF) and cardiac work (WSRP) in the failing heart is shown in red (same results as in FIG. 1); however, the relationship between MBF and WSRP after chromonar (black) shows some important observations. First, note that flow is higher after chromonar treatment.

Second, chromonar treatment reconnects the relationship between work and flow in the heart, meaning that when work increases flow increases. In contrast, the relationship between work and flow in the failing heart, without chromonar, shows a disassociation in that when work increased and flow did not. Taken together, this figure shows that if myocardial blood flow is increased to the failing heart, cardiac function improves.

Another way of assessing the effectiveness of a therapy in heart failure is to determine how much volume is in the left ventricle before it begins to contract (termed diastolic volume). When contractile function of the heart declines, this volume progressively increases. This volume is important for a number of reasons. First, it is directly related to energy consumption of the heart (as the volume increases energy consumption is increased). Second, if this volume becomes too large, the heart muscle can be overstretched and will contract even more poorly—this is referred to as decompensated heart failure. Third, as the diastolic volume increases pressures and volumes "upstream" in the atrium and pulmonary vessels will also increase. This increase in volume in the pulmonary circulation can lead to excess water in the lungs (pulmonary edema) and can cause shortness of breath occurring in heart failure. And finally, this volume, which stretches the heart muscle, can lead to an outward remodeling of the heart, which can be detrimental to function as this leads to poorer contractile function and more energy expenditures. FIG. 3 shows this relationship in mice progressing towards heart failure after transaortic constriction (TAC). This figure parallels the paradigm shown in the left panel of FIG. 2 in that baseline measurements were made and following these measurements TAC was produced to induce heart failure. At the end of week 13, chromonar or vehicle treatments were given to the two groups of mice. The figure shows that after TAC diastolic volumes increased in both groups of animals up to week 13. Then following treatment with chromonar, diastolic volumes decreased; whereas, the diastolic volumes were unchanged in the control, vehicle group. This beneficial result of chromonar treatment corroborates our other findings of increased blood flow, and improved contractile function (ejection fraction) in heart failure.

Methods

Figure 4:
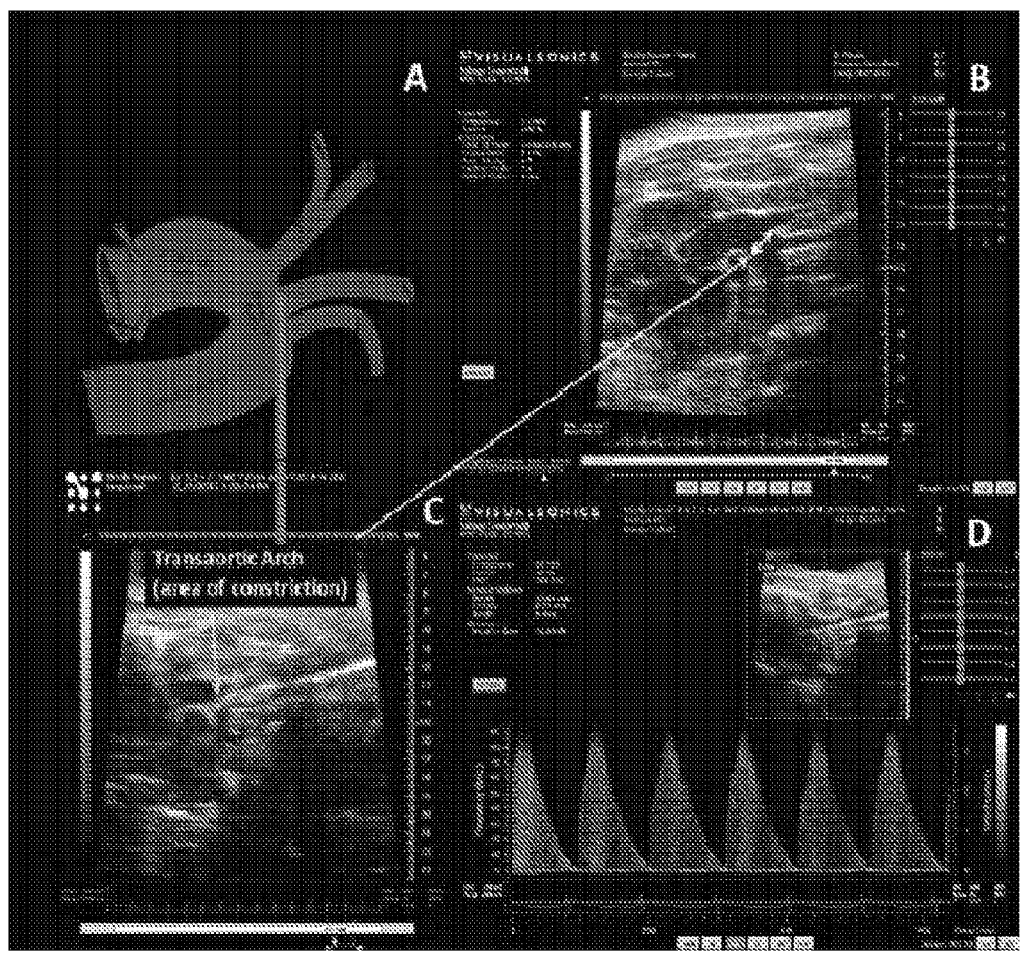
FIGS. 4A-4D provide images showing A. Anatomic structure of the aortic arch; B. Echocardiographic image of aortic arch before TAC; C. Area of constriction after TAC; and D. Flow velocity across the constriction after TAC.
Figure 5:
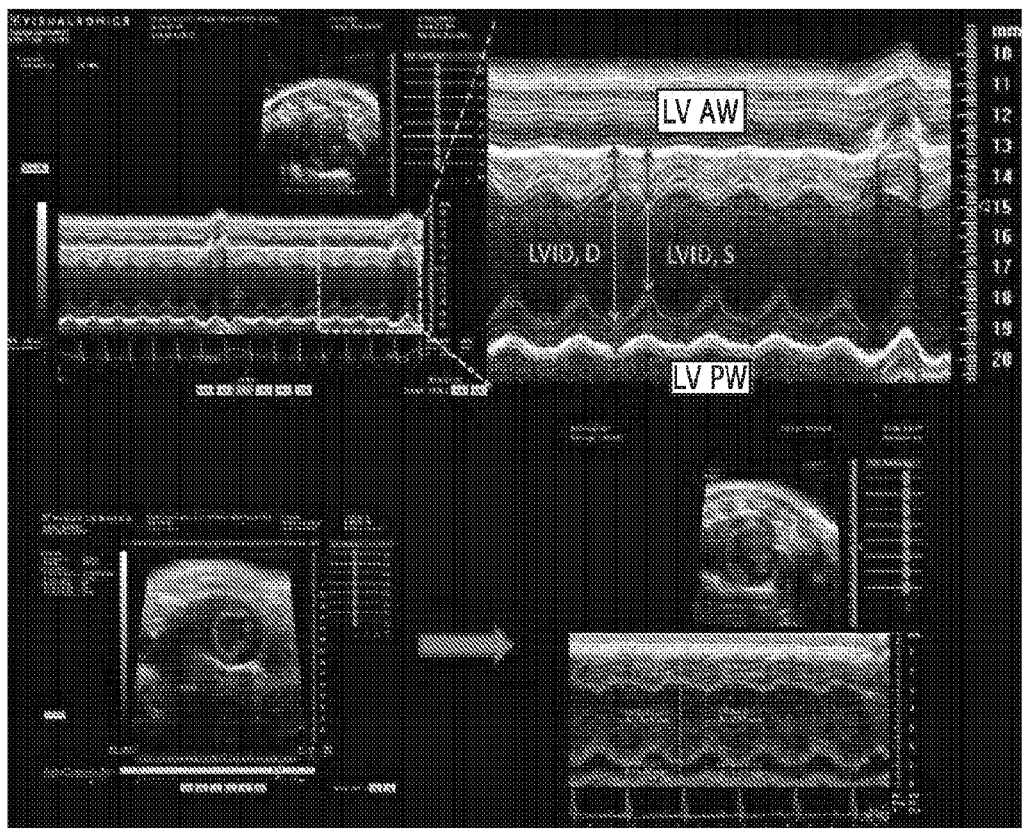
FIG. 5 provides an image showing the Parasternal short axis view and Mmode echocardiography.

Two groups of mice were studied: shams and transaortic constriction (TAC). TAC surgery was performed by tying a suture against a blunt needle (26G), constricting the aorta to approximately 0.4 mm in diameter, and producing a constriction of 65-70%. The surgical preparation and confirmation of the constriction is shown in FIG. 4. Transthoracic echocardiography was done before surgery and weekly in both groups to assess changes in cardiac function. M-mode images were obtained at the level of the mid-papillary muscle (FIG. 5); all calculations were done offline. The degree of constriction was estimated by Doppler echocardiography at the site of the constriction (FIG. 4). The pressure gradient across the constriction was calculated using Bernoulli's equation (pressure gradient=velocity$^2 \times 4$) and averaged 40 mmHg.

Myocardial Blood Flow

Figure 6:
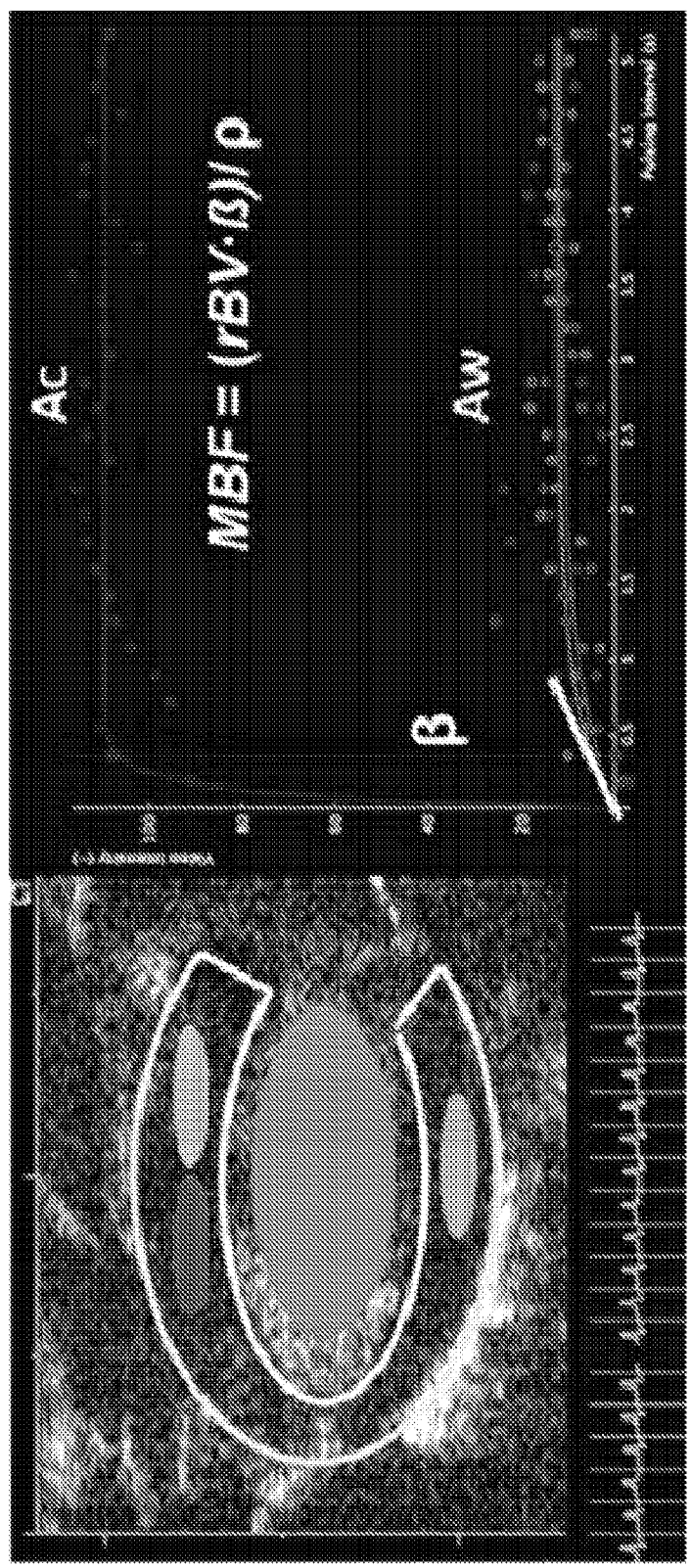
FIG. 6 provides an image showing MCE-derived MBF calculation. The image shows how "regions of interest" (blue, pink, yellow, and green) are selected in the MCE image. The result of these measurements and calculations is an assessment of myocardial blood flow in the mouse left ventricle. The values for beta, the slope, and Aw, the measurement of the contrast in the anterior wall of the heart, are inserted into an algorithm to produce values for myocardial blood flow (MBF) in ml/min per g.

Myocardial contrast echocardiography (MCE) was used to measure myocardial blood flow in both groups of mice. These regions were identified in the contrast images (FIG. 6). Mice were determined to be in HF when EF<40%. After the development of failure, myocardial blood flow was measured during a cardiac stress test produced by infusion of norepinephrine to increase myocardial metabolic demands. A plot of cardiac work vs MBF was made for the sham mice and for those in HF. To estimate metabolic demands, the index wall stress rate product (WSRP) was developed.

Wall stress was used in the calculation of cardiac work, because the left ventricle is dilated in the failing heart; thus, to generate the same pressures as in controls, metabolic demands will be higher when the chamber is dilated. This follows the relationship:

$$WS = P \times r/h$$

Where WS=wall stress, P=Left Ventricular Pressure, r=ventricular diastolic radius, and h=wall thickness.

Example 2: Chromonar Compared with Standard Cardiovascular Agents

Figure 7:
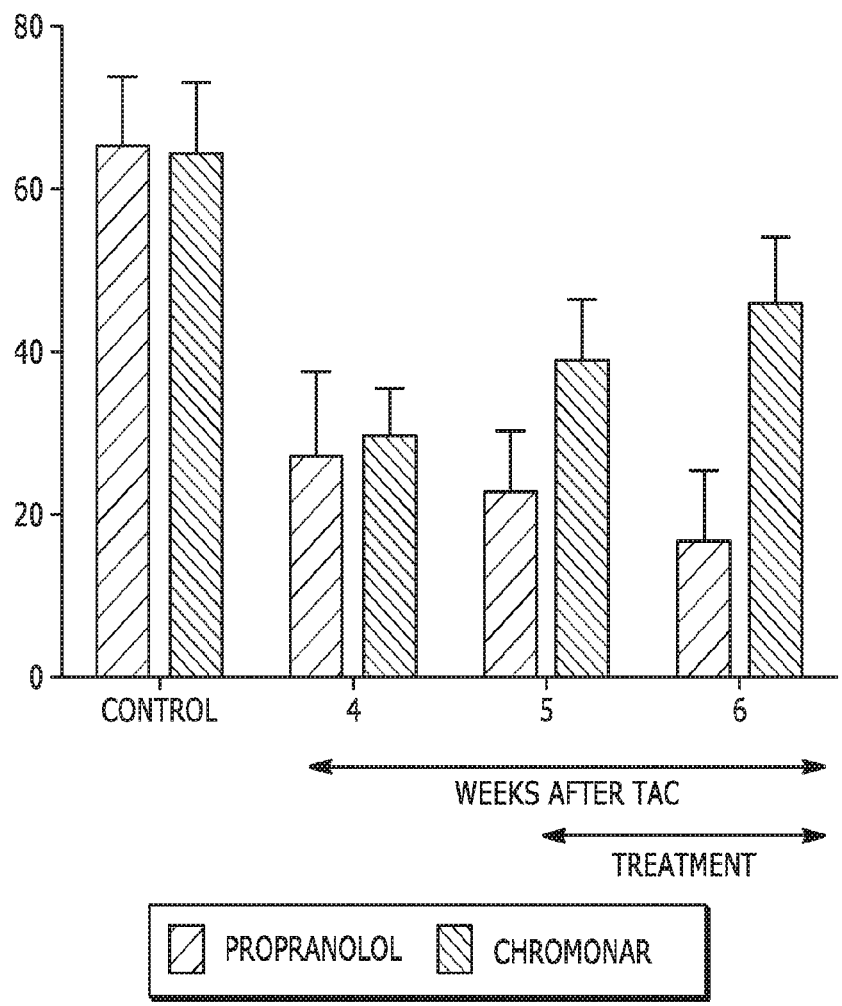
FIG. 7 provides a graph showing a comparison of the effects of propranolol versus chromonar on cardiac function of the failing heart.

The effects of chromonar were then compared to a current "standard of care" used to treat patients in heart failure—a beta-adrenergic antagonist, also known colloquially as a beta-blocker. This comparison is shown in FIG. 7—note that the TAC (transaortic constriction) procedure induces heart failure as shown by the large decrease in cardiac function (EF %; control vs 4 weeks). At week 5 the treatment for heart failure, propranolol (beta-blocker) or chromonar was started. Cardiac function improved dramatically with chromonar, but continued to decrease with propranolol. This suggests that the treatment of heart failure with chromonar has a far better outcome than a current standard of care treatment—a beta-blocker.

Figure 8:
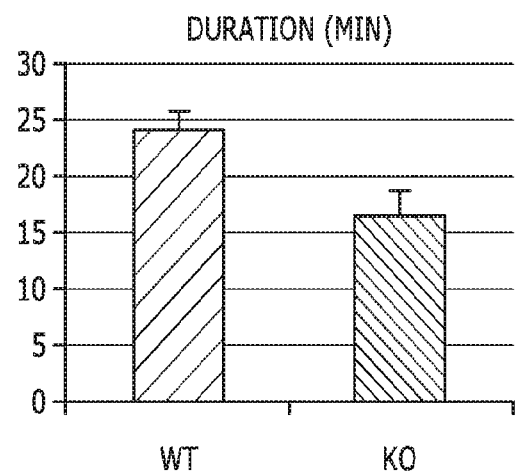
FIG. 8 provides a graph showing the exercise capacity in Wild Type (WT) and Kv1.5 null mice (KO). Exercise capacity is shown as the duration, which is the time to exhaustion, and the maximal exercise capability in the two strains of mice.
Figure 9:
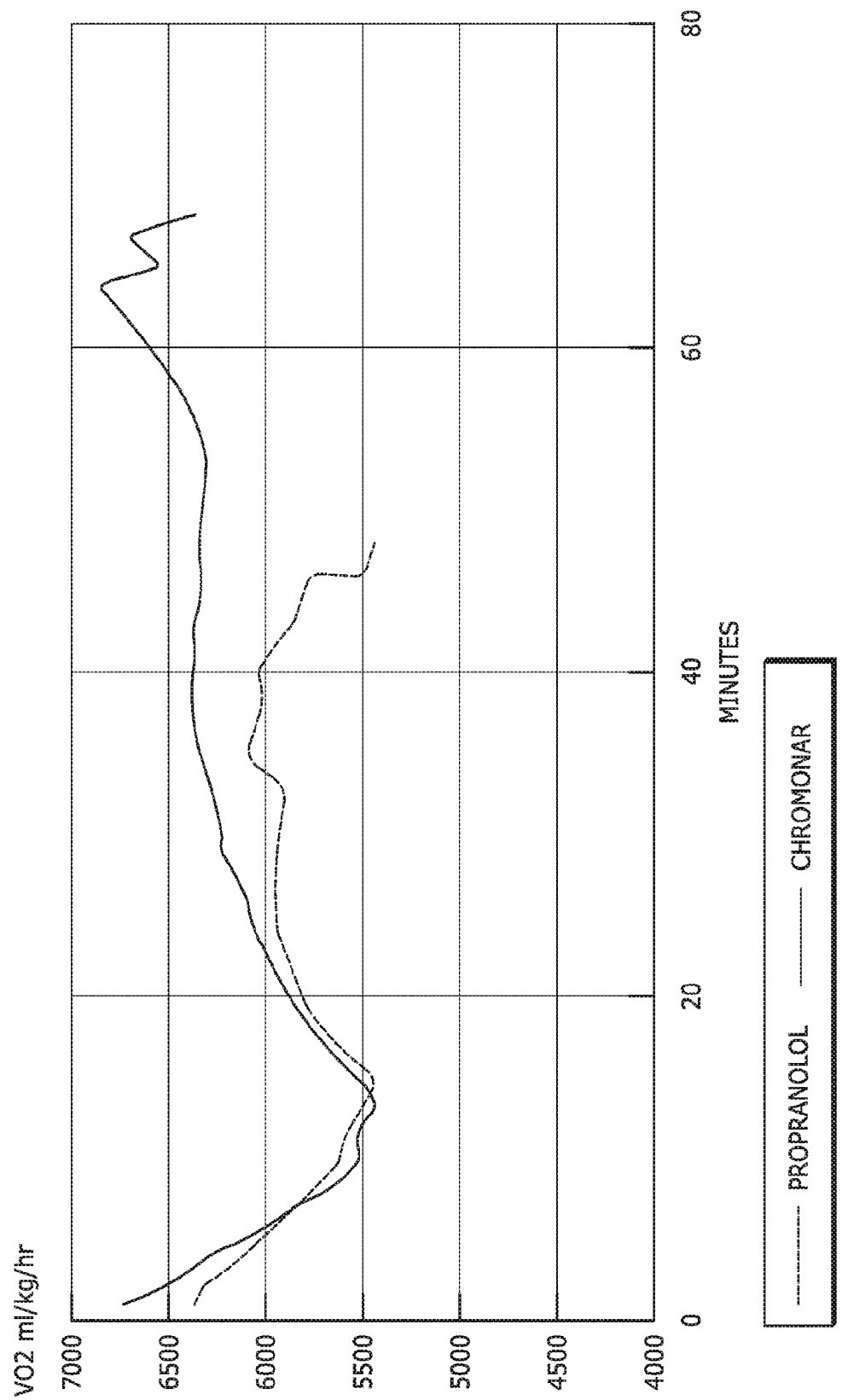
FIG. 9 provides a graph showing the walking times and whole body oxygen consumption in mice in heart failure with preserved ejection fraction (HFpEF) treated with propranolol or chromonar.

FIG. 8 shows results that show implications towards the diseases of INOCA (ischemia no coronary artery disease), MINOCA (myocardial ischemia no coronary artery disease) and HFpEF (heart failure with preserved ejection fraction). The Kv1.5 null mice are a model for HFpEF because they show compromised ventricular diastolic function with ventricular systolic function within normal limits. Although a reduction in diastolic function, in itself, is not a sole indicator of HFpEF other data support the conclusion that Kv1.5 null mice are a model of HFpEF. First Kv.15 null mice have a far shorter lifespan than wild type mice. Most of these mice (>80%) do not live beyond 24 months; whereas close to 100% of wild type mice live well beyond 24 months with about 50% of this strain living to 3 years. Second, a consequence of HFpEF is poor exercise tolerance, which is shown in the two panels of FIG. 8. The Kv1.5 null mice show a poor time it takes to exhaustion, i.e., Kv1.5 null mice cannot exercise as long on a treadmill as their wild type counterparts. Also, their maximal exercise is less. Whereas 100% of the wild type (WT) mice can exercise at 15 meters/min on a treadmill, only 50% of the Kv1.5 null mice are able to cope at this speed. At a higher speed (20 meters/min), none of the Kv1.5 null mice were able to cope at this speed, while 50% of the WT mice were able to run at this speed. Importantly the results shown in FIG. 9 show the impact of chromonar in Kv1.5 null mice. The table included in FIG. 8 shows several attributes of diastolic function of the left ventricle in wild type (WT) and. An important attribute of these mice is that they are a model of INOCA and MINOCA, in that they show symptoms consistent with myocardial ischemia during a cardiac stress test (norepinephrine infusion) in the absence of large vessel disease, i.e., a deficit in microvascular control. During the stress test, cardiac function deteriorates due to the insufficient blood flow and tissue hypoxia due to inadequate blood flow (ischemia which constitutes the "I" in INOCA or MINOCA. The chronic outcome of INOCA or MINOCA is heart failure with preserved ejection fraction (HFpEF).

A popular outcome that is used clinically to demonstrate the effectiveness of a treatment for heart failure is walking time or exercise time. A similar experiment was performed in mice and measured the total time a mouse with heart failure could exercise on a treadmill. Similar to the design in FIG. 7, the goal, shown in FIG. 9, was to compare exercise times and whole body oxygen consumption in mice with heart failure (HFrEF) treated with the beta-blocker, propranolol, versus, chromonar. Note at rest, prior to the start of exercise (minute 15), both groups have similar oxygen consumption. However, within 5 minutes of exercise, the groups diverge in the propranolol treated group shows lower oxygen consumption than the chromonar treated group. Also, note the propranolol treated group could only exercise for about 45 minutes, whereas the mice with chromonar exercised for closer to 70 minutes. Similar to the results on cardiac function, chromonar treatment has a far better effect on exercise time and whole body oxygen consumption than propranolol during heart failure.

Figure 10:
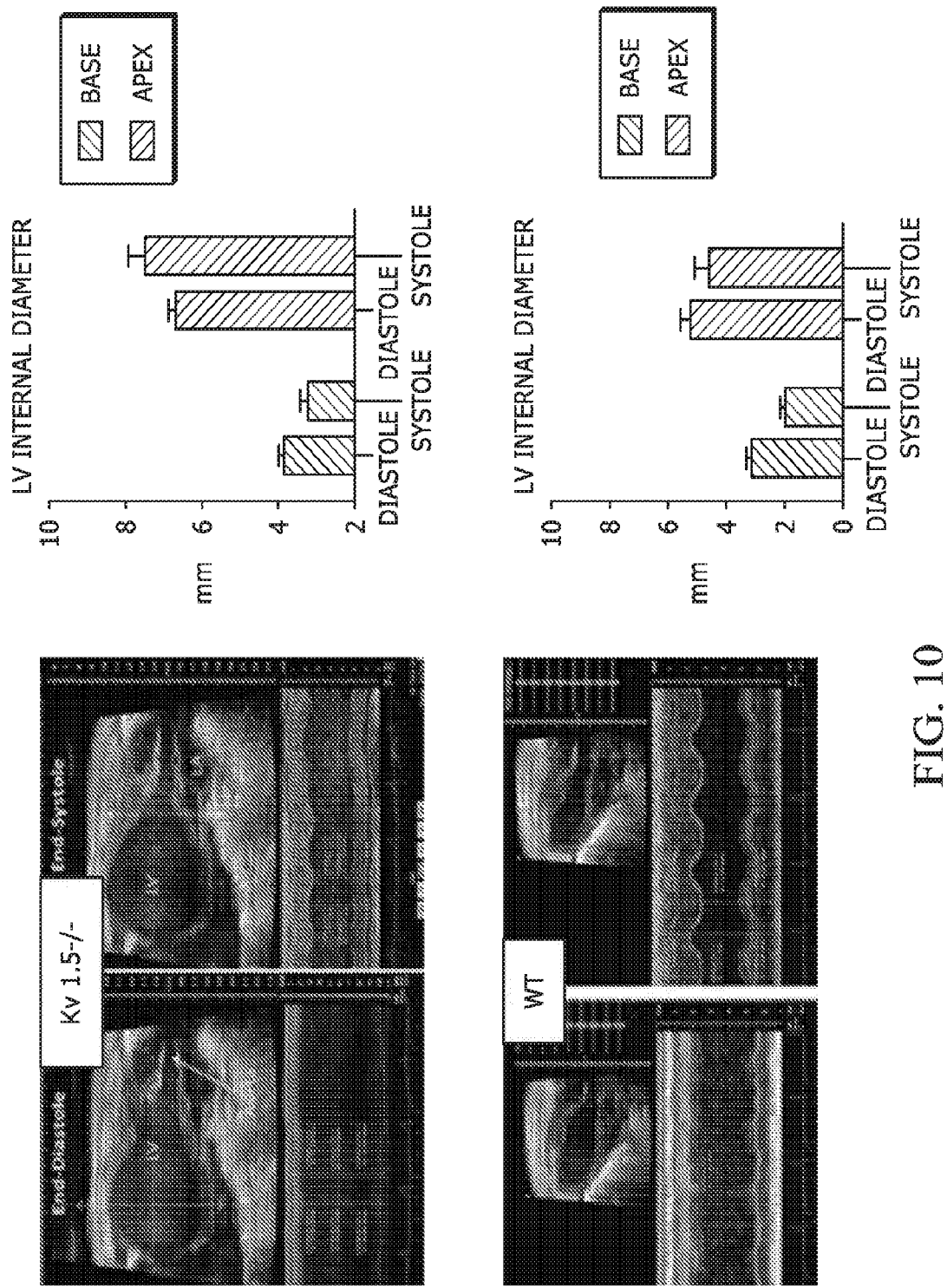
FIG. 10 provides graphs and images showing the Long axis and m-mode echo images in end-diastole and end-systole of the left ventricle of $Kv1.5^{-/-}$ and WT mice subjected to TAC (left). Note the paradoxical ballooning in the $Kv1.5^{-/-}$ mice, which is shown in the aggregate data of internal diameters in end-systole and -diastole on the right. N=3-5

FIG. 10 shows a model of Takotsubo Syndrome, which is also referred to as Apical Ballooning Syndrome, Broken Heart Syndrome, and Stress-Induced Cardiomyopathy. Statistics show that women (over 90% of the cases are women) presenting with this condition are increasing. The inventors emphasize that this syndrome is a conundrum in clinical cardiology in that there is no accepted treatment. Despite not having an accepted standard of care, cardiologists prescribe drugs such as beta-blockers to treat Takotsubo Syndrome without any evidence that such a treatment offers any benefit. The lack of a preclinical model of Takotsubo Syndrome has thwarted development of understanding the mechanism underlying this disorder; however, the inventors have found that in model of INOCA in a particular strain of mice, that if stressed (hypertension, catecholamine) the mice develop Takotsubo Syndrome (FIG. 10). Because the mouse model of Takotsubo Syndrome stems from the inventors model of microvascular disease (INOCA), they proposed that chromonar treatment would offer an effective therapy. This would be important, because currently there is no standard of care for this syndrome and treatments of administered without evidence they are effective.

Figure 11:
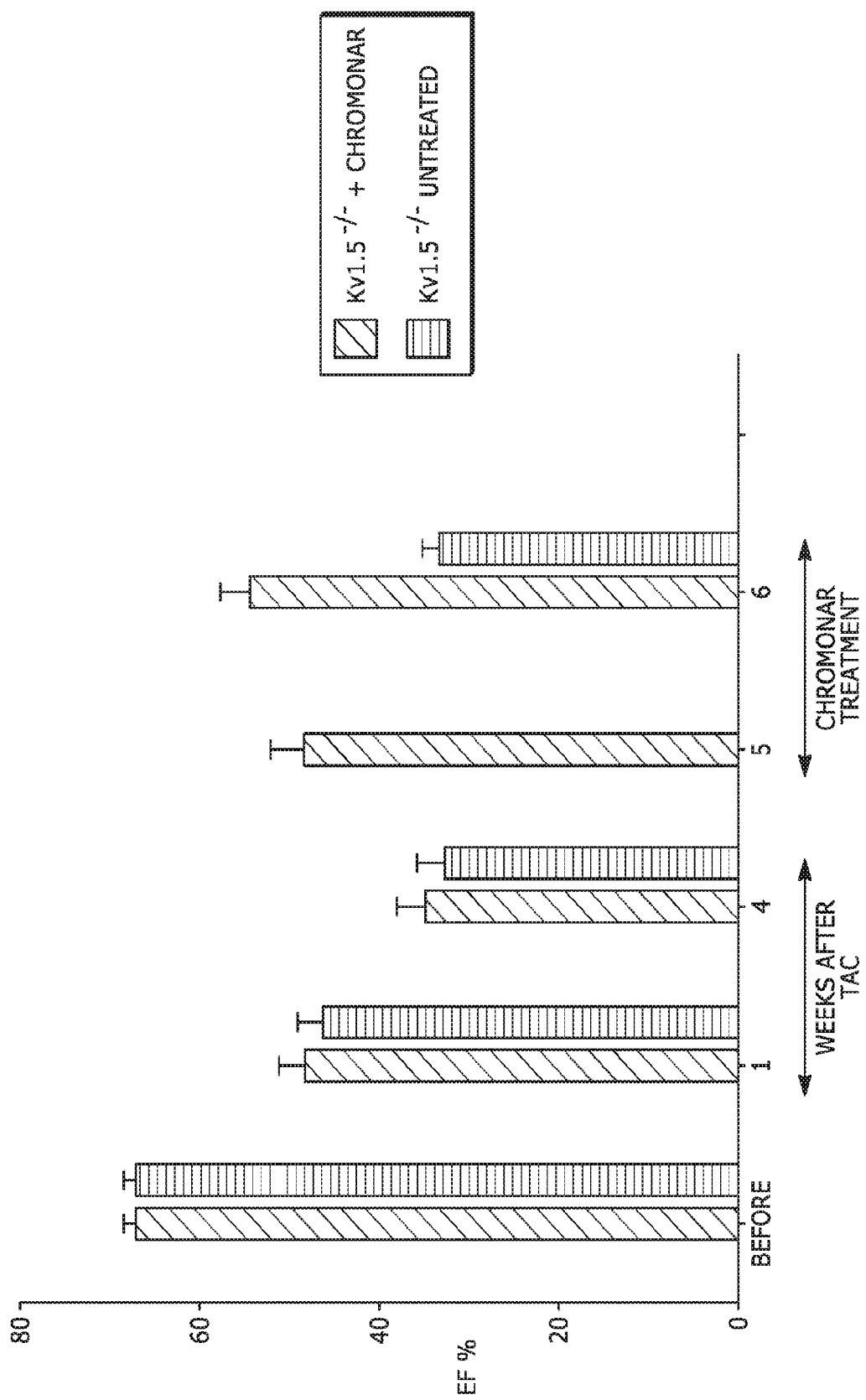
FIG. 11 provides a graph showing the effects of chromonar on ventricular function (EF %) curing Takotsubo Syndrome.

FIG. 11 shows the effects of chromonar on ventricular function during Takotsubo Syndrome. Takotsubo syndrome was produced by transaortic constriction (TAC), which caused a severe depression of ventricular function (EF %) after 4 weeks. Chromonar (2 weeks of treatment) improved ventricular function greatly; whereas the untreated group showed no improvement.

Taken together the findings presented in the Figures support the concept that treatment of heart failure involving blockage of small blood vessels such as Takotsubo Syndrome (and the other names used to describe this condition, e.g, apical ballooning syndrome, broken heart syndrome, stress-induced cardiomyopathy), HFpEF, HFrEF, MINOCA, and INOCA, will benefit from increasing blood flow to the heart with a vasodilator such as chromonar.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for treating heart failure involving blockage of small blood vessels, comprising administering to a subject in need thereof a therapeutically effective amount of a chromonar derivative.

2. The method of claim 1, wherein the chromonar derivative is administered with a pharmaceutically acceptable carrier.

3. The method of claim 1, wherein the heart failure is non-ischemic heart failure.

4. The method of claim 1, wherein the chromonar derivative is administered orally or intravenously.

5. The method of claim 1, wherein, after administration of the chromonar derivative increases myocardial blood flow to the heart of the subject.

6. The method of claim 1, wherein the subject is human.

7. A method for treating Takotsubo Syndrome, comprising administering to a subject in need thereof a therapeutically effective amount of a coronary vasodilator that increases blood flow to the heart without affecting blood flow to other organs.

8. The method of claim 7, wherein the coronary vasodilator is a chromonar derivative.

9. The method of claim 7, wherein the coronary vasodilator is chromonar.

10. The method of claim 7, wherein the coronary vasodilator is dipyridamole.

11. The method of claim 7, wherein the coronary vasodilator is administered with a pharmaceutically acceptable carrier.

12. The method of claim 7, wherein the coronary vasodilator is administered orally or intravenously.

13. A method for treating amyloid cardiomyopathy or amyloidosis of cardiac tissue, comprising administering to a subject in need thereof a therapeutically effective amount of a coronary vasodilator that increases blood flow to the heart without affecting blood flow to other organs.

14. The method of claim 13, wherein the coronary vasodilator is a chromonar derivative.

15. The method of claim 13, wherein the coronary vasodilator is chromonar.

16. The method of claim 13, wherein the coronary vasodilator is dipyridamole.

17. The method of claim 13, wherein the coronary vasodilator is administered with a pharmaceutically acceptable carrier.

18. The method of claim 13, wherein the coronary vasodilator is administered orally or intravenously.

* * * * *